(12) United States Patent
Ye et al.

(10) Patent No.: US 8,850,304 B2
(45) Date of Patent: Sep. 30, 2014

(54) SYSTEM AND METHOD FOR VISUALLY MAPPING AND AUTOMATICALLY COMPLETING ELECTRONIC FORMS

(75) Inventors: Qin Ye, Castaic, CA (US); Darius Lezama, Huntington Beach, CA (US); Matthew J. Haddad, Marina del Rey, CA (US)

(73) Assignee: Kip Medv PI LP, New York, NY (US)

( * ) Notice: Subject to any disclaimer, the term of this patent is extended or adjusted under 35 U.S.C. 154(b) by 220 days.

(21) Appl. No.: 13/022,550

(22) Filed: Feb. 7, 2011

(65) Prior Publication Data

US 2011/0197119 A1      Aug. 11, 2011

Related U.S. Application Data

(60) Provisional application No. 61/302,050, filed on Feb. 5, 2010.

(51) Int. Cl.
*G06F 17/24* (2006.01)
*G06Q 30/08* (2012.01)
*G06Q 50/22* (2012.01)

(52) U.S. Cl.
CPC .............. *G06Q 50/22* (2013.01); *G06Q 30/08* (2013.01)
USPC ........................... 715/226; 715/224; 715/225

(58) Field of Classification Search
CPC .............. G06F 17/243; G06F 17/2247; G06F 17/30569
USPC .......................................... 715/225, 226, 224
See application file for complete search history.

(56) References Cited

U.S. PATENT DOCUMENTS

| | | | |
|---|---|---|---|
| 6,216,131 B1 * | 4/2001 | Liu et al. ............................... | 1/1 |
| 6,854,085 B1 * | 2/2005 | Morse ........................... | 715/236 |
| 7,603,301 B1 | 10/2009 | Regan | |
| 8,214,362 B1 * | 7/2012 | Djabarov ....................... | 707/736 |
| 2002/0120628 A1 * | 8/2002 | Hitchcock et al. ............. | 707/100 |
| 2002/0161605 A1 * | 10/2002 | Newman et al. .................... | 705/2 |
| 2004/0117617 A1 * | 6/2004 | Geller et al. ................... | 713/156 |
| 2004/0181749 A1 | 9/2004 | Chellapilla et al. | |
| 2005/0028082 A1 * | 2/2005 | Topalov et al. ............... | 715/505 |
| 2005/0149854 A1 | 7/2005 | Pennell et al. | |

(Continued)

OTHER PUBLICATIONS

International Search Report and Written Opinion of the International Searching Authority, dated Mar. 30, 2011, corresponding to International Application PCT/US11/23948, 7 pages.

*Primary Examiner* — Stephen Hong
*Assistant Examiner* — Ahamed I Nazar
(74) *Attorney, Agent, or Firm* — Baker Hostetler LLP

(57) ABSTRACT

A computer apparatus and method are provided for visually mapping fields of various electronic forms to a common object model. The forms may then be dynamically completed via a runtime engine that retrieves mapping data from a relational database and uses the mapping data to automatically populate corresponding fields of the forms without manual input by the user. Specifically, a visual mapping tool displays the objects of the common object model as well as the fields of a form to be mapped. A user drags and drops one or more of the displayed objects into a mapping area, and drags and drops a field to which the one or more objects are to be mapped. The user also identifies a type of association between the selected objects and the field. A mapping entry is then generated in a map file to map the selected objects to the field.

18 Claims, 13 Drawing Sheets

(56) References Cited

U.S. PATENT DOCUMENTS

| | | | |
|---|---|---|---|
| 2005/0256841 A1* | 11/2005 | Rawat et al. | 707/1 |
| 2006/0036634 A1* | 2/2006 | Kristiansen et al. | 707/102 |
| 2007/0157096 A1* | 7/2007 | Keren et al. | 715/760 |
| 2008/0134089 A1* | 6/2008 | Adachi et al. | 715/810 |
| 2008/0313529 A1* | 12/2008 | Gwozdz et al. | 715/224 |
| 2009/0076966 A1 | 3/2009 | Bishop et al. | |

* cited by examiner

SYSTEM AND METHOD FOR VISUALLY MAPPING AND AUTOMATICALLY COMPLETING ELECTRONIC FORMS

CROSS-REFERENCE TO RELATED APPLICATIONS

This application claims the benefit of U.S. Provisional Application No. 61/302,050, filed Feb. 5, 2010, the content of which is incorporated herein by reference.

This application is also related to U.S. Application entitled "System and Method for Peer Referencing in an Online Computer System" Ser. No. 13/022,604, filed on even date herewith, and to U.S. Pat. No. 7,529,682, the content of both of which are incorporated herein by reference.

FIELD OF THE INVENTION

The present invention generally relates to systems and methods for managing and completing electronic forms, and more particularly, to a system and method for mapping healthcare administrative forms to a common object model for automating the completion of such forms.

BACKGROUND

There is a general need for mapping healthcare data, especially healthcare provider information, such as demographics, license, education, and billing information, to enable the populating of administrative forms. Healthcare providers (also referred to as doctors or practitioners) are often required to fill out hundreds of various forms that are exchanged with other providers and healthcare entities to maintain their practice as well to maintain insurance and hospital affiliations. For example, a specialist applying for credentialing may need to complete a form for one healthcare entity that contains the same core information he or she just filled in a different form used to apply for enrollment and contracting for another healthcare entity.

One common method of auto-completing or pre-populating forms is one-to-one mapping of database fields to form fields, via manual coding. Such mapping generally requires re-mapping, at a programming level, of each relationship as new forms are added to the system. As the result, the process may take weeks to map one form and does not provide reasonable scalability to deal with the vast amount different forms in the healthcare industry.

Another method for pre-populating forms includes extracting data from a database into a separate flat file. An offline form mapping tool is then utilized to map form fields with flat file data fields to eventually populate the form with extracted data. This process is also cumbersome and time consuming due to lack of automation and reusability.

Accordingly, there is a need for a system and method for automating the mapping and completion of different forms that is more efficient and more scalable than existing methodologies.

SUMMARY

According to one embodiment, the present invention is directed to a computer apparatus and a method for mapping fields of an electronic form to a common object model. The computer apparatus includes a data storage device, a display device displaying a mapping area, a processor, and a memory that is operably coupled to the processor and that stores program instructions therein. The processor is operable to execute the program instructions. The program instructions include displaying on the display device a plurality of objects of the common object model, and displaying on the display device a plurality of fields of the electronic form. The program instructions further include receiving user selection of one or more of the displayed objects of the common object model, and displaying the selected one or more objects in the mapping area. User selection of one of the displayed fields of the electronic form is also received, and the selected field is displayed in the mapping area. The program instructions further include identifying a type of association between the one or more objects in the mapping area, and the field in the mapping area. The program instructions then generate a mapping entry in a map file of the data storage device, mapping the one or more objects in the mapping area, to the field in the mapping area. The mapping entry includes the identified type of association. The map file is then configured to be retrieved for automatically populating the plurality of fields of the electronic form with data stored for the objects mapped to the plurality of fields.

According to one embodiment of the invention, the user selection of the one or more of the displayed objects includes dragging and dropping the selected one or more of the objects to the mapping area. Similarly, the user selection of one of the displayed fields includes dragging and dropping the displayed field to the mapping area.

According to one embodiment of the invention, the displaying the plurality of objects includes displaying identifiers for the objects in a list format.

According to one embodiment of the invention, the identifying the type of association includes displaying a list of associations, and receiving a user selection of one of the associations from the list.

According to one embodiment of the invention, the type of association indicates a direct mapping between a single object in the mapping area, and the field in the mapping area.

According to one embodiment of the invention, the type of association indicates mapping a plurality of the objects in the mapping area, to the field in the mapping area.

According to one embodiment of the invention, the type of association identifies an aggregation rule for aggregating data stored for the plurality of objects in the mapping area, when populating the field on the form mapped to the plurality of objects.

According to one embodiment of the invention, the type of association identifies a conversion rule for converting an aspect of data stored for the one or more objects in the mapping area, when populating the field on the form mapped to the one or more objects. The converting may be converting a format of the data.

According to another embodiment, the present invention is also directed to a computer apparatus and method for automatically populating an electronic form. The computer apparatus includes a data storage device storing a plurality of forms and a map file for each of a plurality of forms. Each of the forms includes one or more fields. The computer apparatus also includes a display device, a processor, and a memory operably coupled to the processor. The memory stores program instructions for being executed by the processor. The program instructions include populating a common object model based on the received data, receiving user selection of a form in the data storage device to be populated, and retrieving a map file for the selected form from the data storage device. The map file maps each of the one or more fields of the form to one or more objects of the common object model, and further indicates a type of association for each mapping. The program instructions also include retrieving data stored for the one or more objects of the common object model mapped to the one or more fields of the form, and processing the retrieved data based on the type of association indicated for the retrieved data in the retrieved map file. The program instructions then automatically populate the one or more fields of the form based on the processed data. The populated fields are then displayed on the display device.

According to one embodiment of the invention, the program instructions further include displaying a universal form corresponding to the common object model, and prompting the user to enter information requested on the universal form.

According to one embodiment of the invention, the automatically populating the one or more fields based on the processed data is without manual input of the data by the user into the one or more fields of the form.

These and other features, aspects and advantages of the present invention will be more fully understood when considered with respect to the following detailed description, appended claims, and accompanying drawings. Of course, the actual scope of the invention is defined by the appended claims.

BRIEF DESCRIPTION OF THE DRAWINGS

FIG. 8 is screen shot of an exemplary screen for mapping objects of a common object model to fields of a form, according to one embodiment of the invention;

FIG. 9 is a screen shot of an exemplary screen displaying a form that has been selected for mapping, according to one embodiment of the invention;

FIG. 10 is a screen shot of an exemplary screen with a list of conversion options in a conversion drop down list, according to one embodiment of the invention;

FIG. 12 is a screen shot of an exemplary mapping table of a map file according to one embodiment of the invention; and FIG. 13 is a screen shot of the form depicted in FIG. 9, with exemplary data filled in according to the mapping schema in the mapping table of FIG. 12, according to one embodiment of the invention.

DETAILED DESCRIPTION

Embodiments of the present invention are directed to a visual mapping tool for visually mapping various healthcare administrative forms to a common healthcare object model. Those forms may then be dynamically completed via a runtime form processing engine (referred to as a runtime engine) that retrieves data stored in a relational database and uses the mapping data to automatically populate corresponding fields of the forms without manual input by the user. Specifically, embodiments of the present invention are directed to a healthcare common object model linked to a relational database, a visual mapping tool that facilitates automated mapping of the healthcare common object model to healthcare administrative forms, and a generated map file that is employed to facilitate and further automate form mapping and form population processing on a large scale.

Specifically, embodiments of the present invention provide a visual mapping tool that displays the objects of the common object model as well as the fields of a form to be mapped. A user drags and drops one or more of the displayed objects into a mapping area, and drags and drops a field to which the one or more objects are to be mapped. The user also identifies a type of association between the selected objects and the field. A mapping entry is then generated in a map file to map the selected objects to the field.

A person of skill in the art should recognize that the present system and method for visual object mapping and automated forms completion provide a streamlined and transparent process for mapping, retrieving, and pre-populating forms. According to one embodiment, the visual mapping tool provides linkage between form fields and business objects without requirement of any programming from the business users. The object model and runtime engine perform dynamic read operations on the database and utilize mapped configuration files to complete specific forms without any additional manual programming. Furthermore, changes to the underlying data model typically do not necessitate additional mapping.

Figure 1:
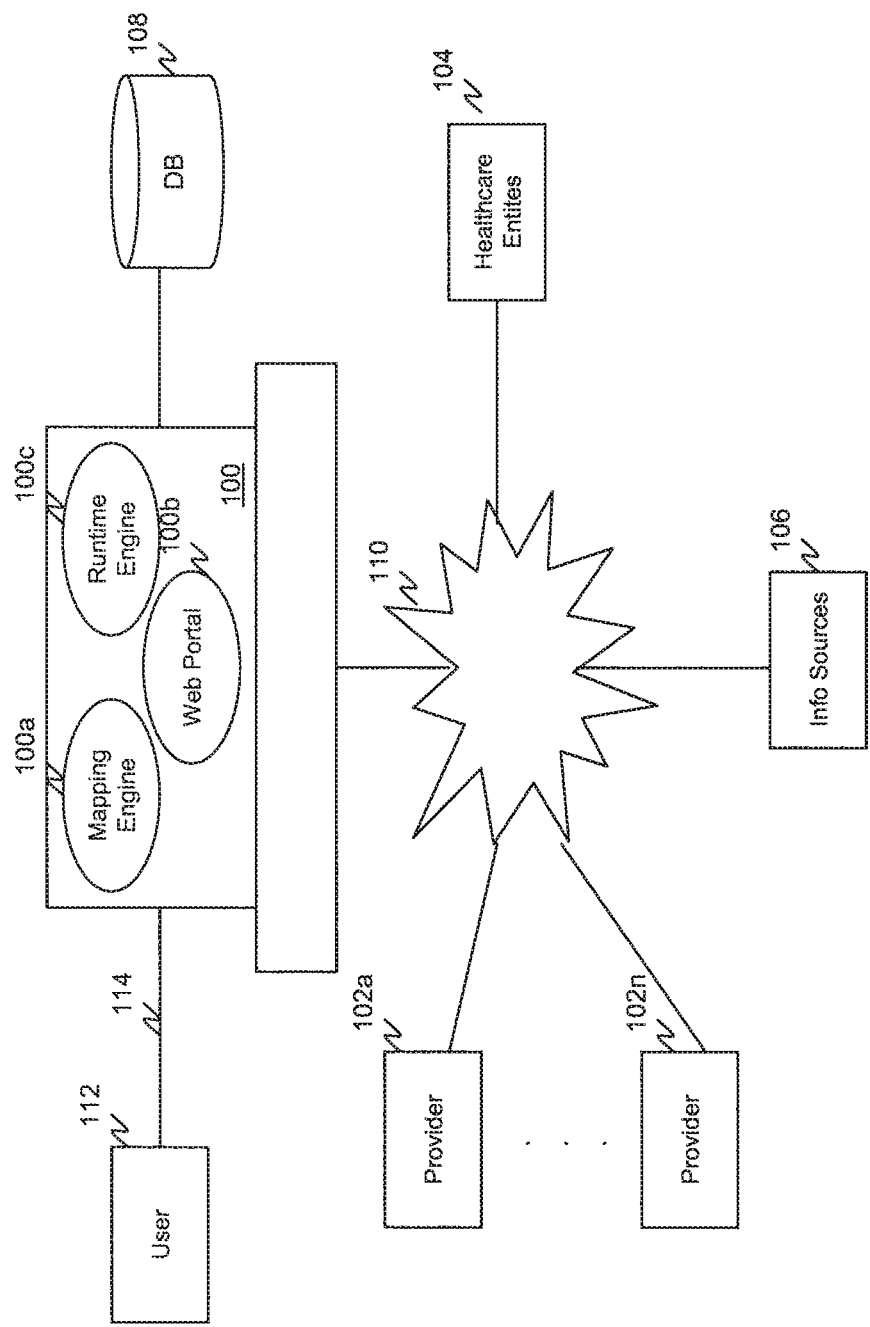
FIG. 1 is a block diagram of a system and method for visually mapping and automatically completing electronic forms according to one embodiment of the invention.

FIG. 1 is a block diagram of a system and method for visually mapping and automatically completing electronic forms 10 according to one embodiment of the invention. The system includes one or more remote healthcare provider devices 102a-102n, healthcare entity devices 104, and information sources 106 (collectively referred to as remote devices), coupled to one or more servers 100 over a data communications network 110. The communication network 110 may be a network or combination of networks spanning any geographical area, such as a local area network, wide area network, regional network, national network, and/or global network. The Internet is an example of a current global computer network. In addition, the communication network may be a hardwire network, wireless network, or a combination of hardwire and wireless networks.

Hardwire networks may include, for example, fiber optic lines, cable lines, ISDN lines, copper lines, and the like. Wireless networks may include, for example, cellular systems, personal communications service (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

Each of the remote devices may be any processor controlled device that permits access to the communication network 110, including terminal devices, such as personal computers, workstations, servers, clients, mini-computers, mainframe computers, laptop computers, a network of individual computers, mobile computers, palm-top computers, handheld computers, set top boxes for a television, other types of web enabled televisions, interactive kiosks, personal digital assistants, interactive or web enabled wireless communications devices, mobile web browsers, or a combination thereof. In this regard, the remote devices include a processor, memory, and one or more input devices such as a keyboard, mouse, touch pad, joystick, pen input pad, and the like. The remote devices may also include an output device, such as a display screen and audio output. The memory included in each remote device stores computer program instructions which, when executed by the processor, causes the processor to perform certain actions mandated by the computer program instructions. Such computer program instructions may also be stored in a disk, CD, or other secondary storage device.

The server 100 may be similar to the server described in the above-referenced U.S. Pat. No. 7,529,682. The server 100 may be hosted by a particular healthcare entity such as, for example, an insurance company, hospital, surgical center, or the like. According to one embodiment, the server may be configured to provide the electronic credentials verification and management functionalities described in U.S. Pat. No. 7,529,682. The server 100 is also configured to map various healthcare administrative forms to a common object model, and automatically populate those forms based on data provided by a healthcare provider or other information source. The server 100 also hosts various web portals for access by different providers, healthcare entities, administrators, and the like. For example, a provider portal allows a provider to create and maintain his profile and credentialing data for verification, forms generation, and the like. A peer network portal allows providers to create a peer network of providers for peer referral and the like, as is described in further detail in the above-referenced U.S. Application entitled "System and Method for Peer Referencing in an Online Computer System." Administrators may access the web portal to map administrative to a common object model, respond to requests for approval of mapped forms, and the like.

In this regard, the server includes a mapping engine 100a, one or more web portals 100b, and a runtime engine 100c. The mapping and run-time engines and the web portals may be implemented as software modules that are executed by a processor in the server based on computer program instructions stored in memory. The mapping and run-time engines may each be a separate software module, or one or more of the engines may be combined into a single module or further divided into one more sub-modules as may be appreciated by a person of skill in the art. A person of skill in the art should also recognize that the engines may be implemented in hardware, firmware (e.g. ASIC), or a combination of hardware, firmware, and/or software.

The data storage device 108 may be any hard disk drive or drive array which hosts a number of purpose-built databases and files useful for implementation of the system 10. For example, the data storage device may take the form of a hard disk or disk array, storing a provider's profile, credentialing information, networking database with information on the provider's peer network, healthcare forms, map files, object model, and information of other entities associated with the system. Any electronic healthcare form may be mapped and stored in the data storage device. Such exemplary forms include, but are not limited to enrollment forms, credential forms, medical claims, information forms, and the like. Of course, a person of skill in the art should recognize that the present invention is not limited to the healthcare field. Hence, the forms that are stored and mapped for auto-completion may vary depending on the field in which the present invention is utilized.

According to one embodiment of the invention, a user device 112 is coupled to the server 100 via a communications link 114. The user device 112 may be similar any of the remote devices described above. The communications link 114 may be a direct wire, an infrared data port, a wireless communications link, global communications link such as the Internet, or any other communications medium known in the art.

According to one embodiment, the user device 112 accesses the mapping engine 100a hosted by the server 100 for mapping various healthcare forms to a common object model, such as, for example, a healthcare object model, as described in further detail below. The access may be via a graphical user interface (GUI) provided, for example, by the mapping engine 100a or some other user interface engine. Alternatively, the access may be via the web portal 100b accessed over the Internet. The user device 112 may also access an administrative portal for approving a map file generated upon mapping of a particular form, as well as to engage in different administrative functions. The administrative portal may be provided as part of the web portal 100b for access over the Internet. A user accessing the user device 112 may be, for example, a provider, healthcare entity, administrator, or anyone with authority to create or edit a map file.

According to one embodiment of the invention, the mapping engine 100 provides a visual mapping tool to enable detailed mapping between a common healthcare business object model to field objects contained in various electronic forms (e.g. PDF, XPS, Word template, web page, and the like). The mapping tool may provide one or more graphical user interface screens for guiding a user through the mapping process, and may identify a specific type and version of the form to the mapped, the fields in the form, and the relationships to each object in the healthcare object model. According to one embodiment, the common object model represents real life entities, e.g. provider practice types, licenses, certifications, etc. Thus, the intended mapping user can easily follow the object structure and drag-and-drop each object, attribute, and/or property (collectively referred to as an object) for a corresponding field object of the form being mapped, via the graphical user interface. Each completed mapping process produces a structured map file in XML or other standard format with detailed metadata that stores a reference to the specific form that was mapped. The map file and related metadata is then stored in the data storage device 108.

Figure 2:
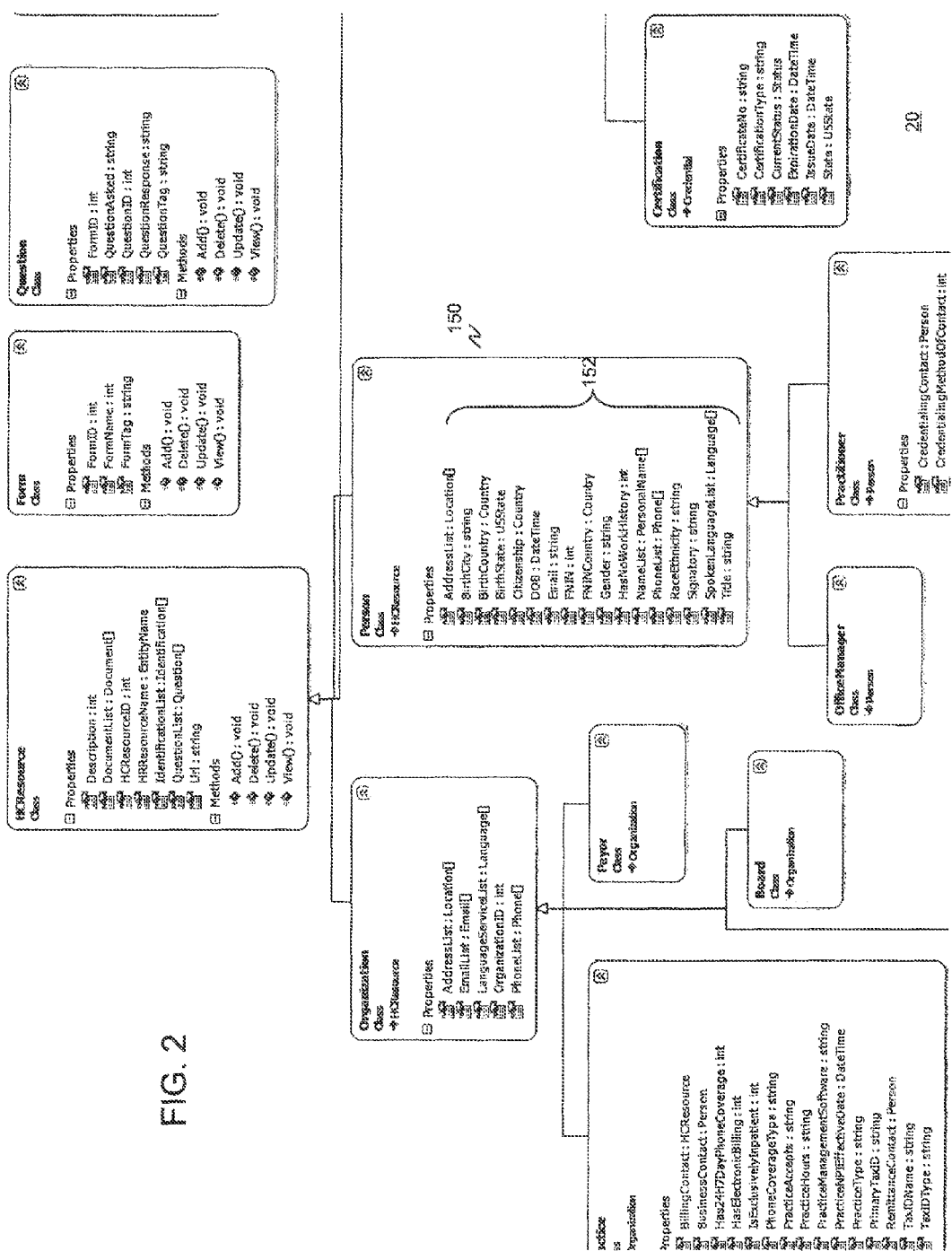
FIG. 2 is a schematic layout diagram of an exemplary common healthcare class object model according to one embodiment of the invention.

FIG. 2 is a schematic layout diagram of an exemplary common healthcare class object model 20. According to one embodiment, the model is organized around common administrative processes, although other types of organization formats will be readily apparent to a person of skill in the art. General healthcare entity information (e.g. doctors, providers, healthcare organizations, insurance companies, hospitals, license, address, affiliations, etc.) are represented as classes/objects 150. The detailed information for each entity is represented by the object's attributes/properties 152. The relationships of these entities are captured with HL-7 compliant relations. The common class object model can in turn dynamically generate a data access layer that may be accessed to create, read, update, and delete (CRUD) information stored with respect to the object model, upon request, via conventional mechanisms known in the art.

According to one embodiment of the invention the runtime engine 100c retrieves a specific map file as soon as a system or user requests auto completion of any form selected from a pre-mapped form library. The runtime engine is configured to retrieve the exact map file for the selected form using the metadata and unique identifier associated with the map file. An execution component of the runtime engine uses the metadata and map file to derive form fields and corresponding instances of each related object, and instantiates the data access layer for dynamic data retrieval from the common object model.

Figure 3:
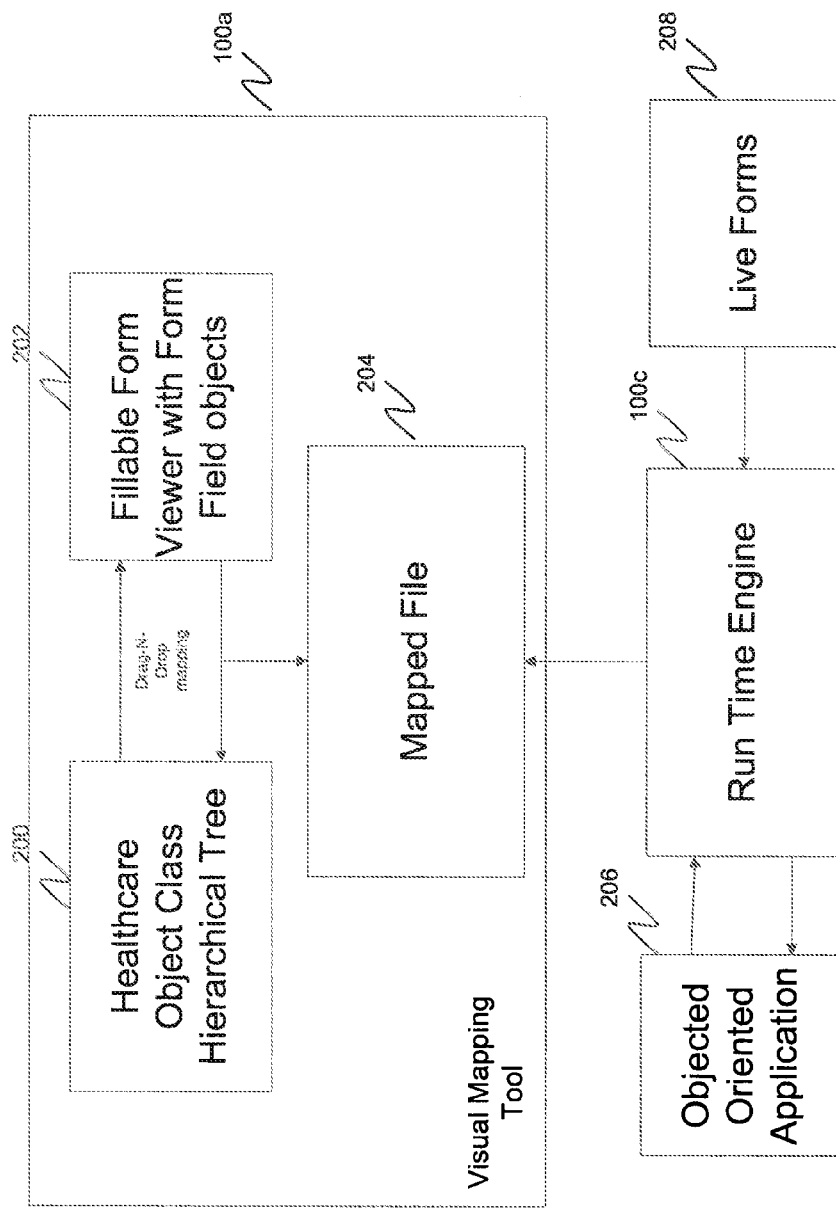
FIG. 3 is a functional block diagram of a mapping engine and a runtime engine according to one embodiment of the invention.

FIG. 3 is a functional block diagram of the mapping engine 100a and the runtime engine 100c according to one embodiment of the invention. The mapping engine 100a visually displays a hierarchical tree 200 representative of a healthcare object class on a display coupled to a remote device, such as, for example, on the user device 112. The mapping engine further displays on the device a form to be mapped to the object class. As the mapping user invokes a mouse, keyboard, keypad, etc., of his or her user device 112 to drag and drop model objects to map to corresponding field objects in the displayed form, associations are formed between the objects and the form fields. The association is stored in a map file 204 which in turn is stored in the data storage device.

When a healthcare provider submits a request to generate a form, such as, for example, via the provider device 102 which submits the request via the web portal 100b, the request is forwarded to the runtime engine 100c. The runtime engine 100c retrieves the requested form 208 from a database of forms stored in the data storage device 108. The runtime engine further invokes an object oriented application 206 that accesses the data access layer of the common object model to retrieve data stored for the provider according to the object model, and further uses the map file 204 for the requested form 208 to automatically populate the fields of the form. For example, the data to be automatically populated on the form may be the provider's credentialing data which the provider may have already provided for filling out a different form.

Figure 4:
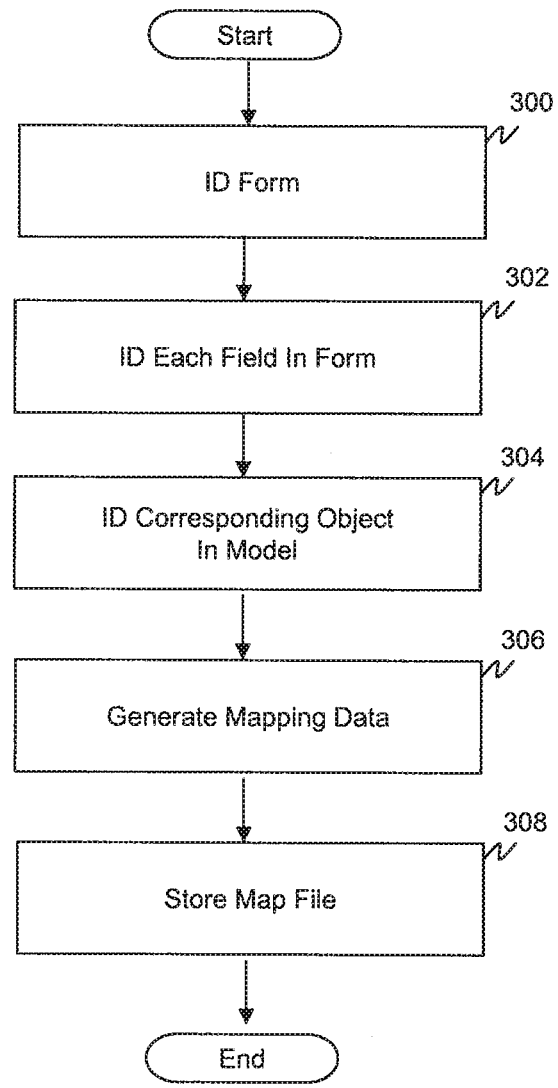
FIG. 4 is a flow diagram of a process executed by a mapping engine to generate a map file according to one embodiment of the invention.

FIG. 4 is a flow diagram of a process executed by the mapping engine 100a to generate a map file according to one embodiment of the invention. The process may be described in terms of a software routine executed by the processor in the server 100 based on instructions stored in the server's memory. A person of skill in the art should recognize, however, that the routine may be executed via hardware, firmware (e.g. via an ASIC), or in any combination of software, firmware, and/or hardware. Furthermore, the sequence of steps of the process is not fixed, but can be altered into any desired sequence as recognized by a person of skill in the art.

Figure 8:
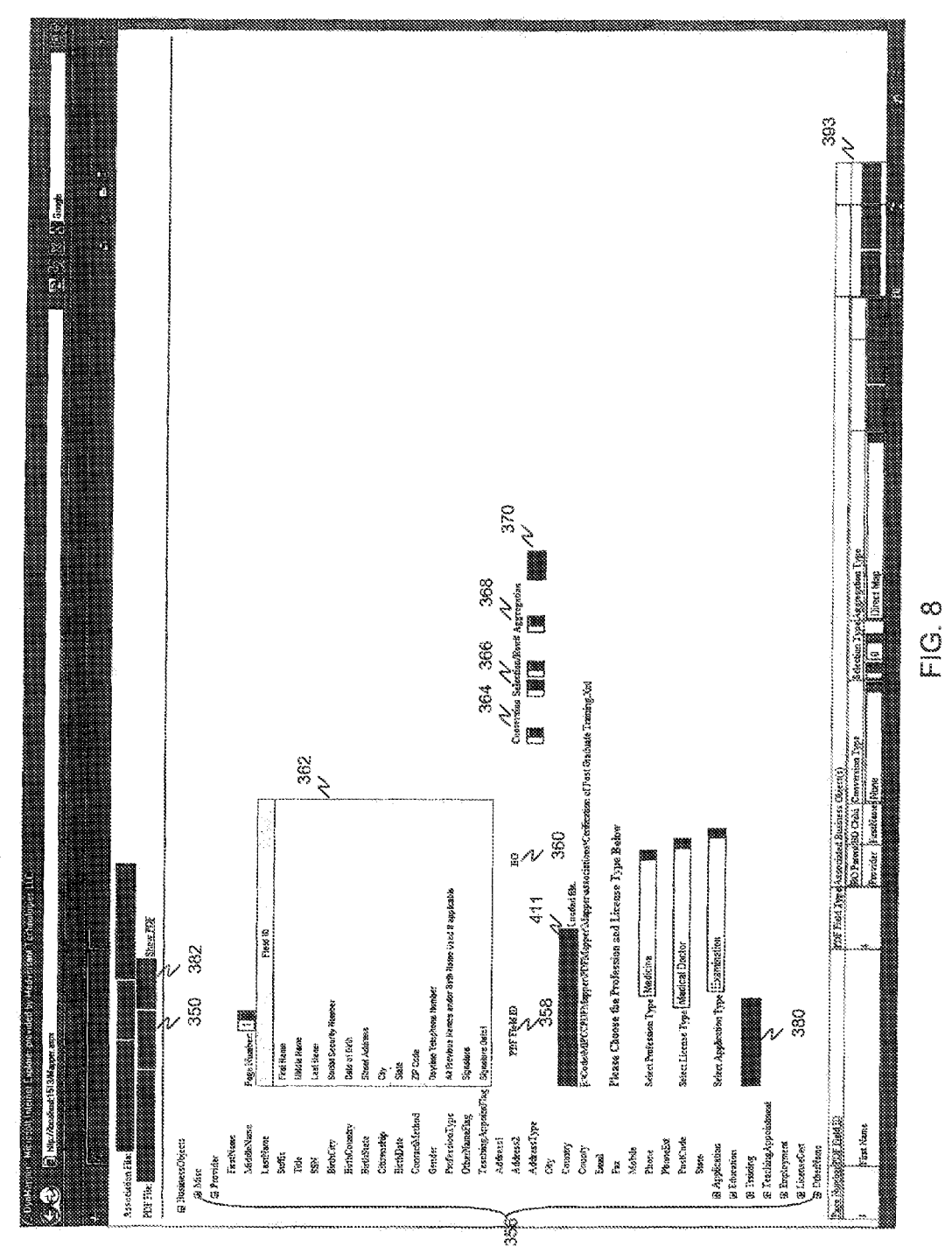

In step 300, the mapping engine 100a receives identification of a form to be mapped. In this regard, the mapping engine invokes a GUI to display a GUI screen on the user device 112, such as the GUI screen depicted in FIG. 8. The GUI screen of FIG. 8 provides, a browse button 150 which, upon selection, displays a list of forms stored in the forms database of the data storage device 108. According to one embodiment, a most recent version of each form is displayed upon selection of the browse button. Alternatively, all versions of the forms may be displayed. The forms may be organized in the forms database according to any category, such as, for example, health plans, types of forms (e.g. enrollment, credential, claim, information, etc.), and the like. Each form may be associated with a status indicating whether the form has been mapped, awaiting approval of mapped data, and the like. According to one embodiment, each form is stored in a data storage device along 108 with a unique form ID. In addition, each form is further associated with an encoding file, such as, for example, an XML, file, identifying the various field names along with their unique field IDs.

Figure 9:
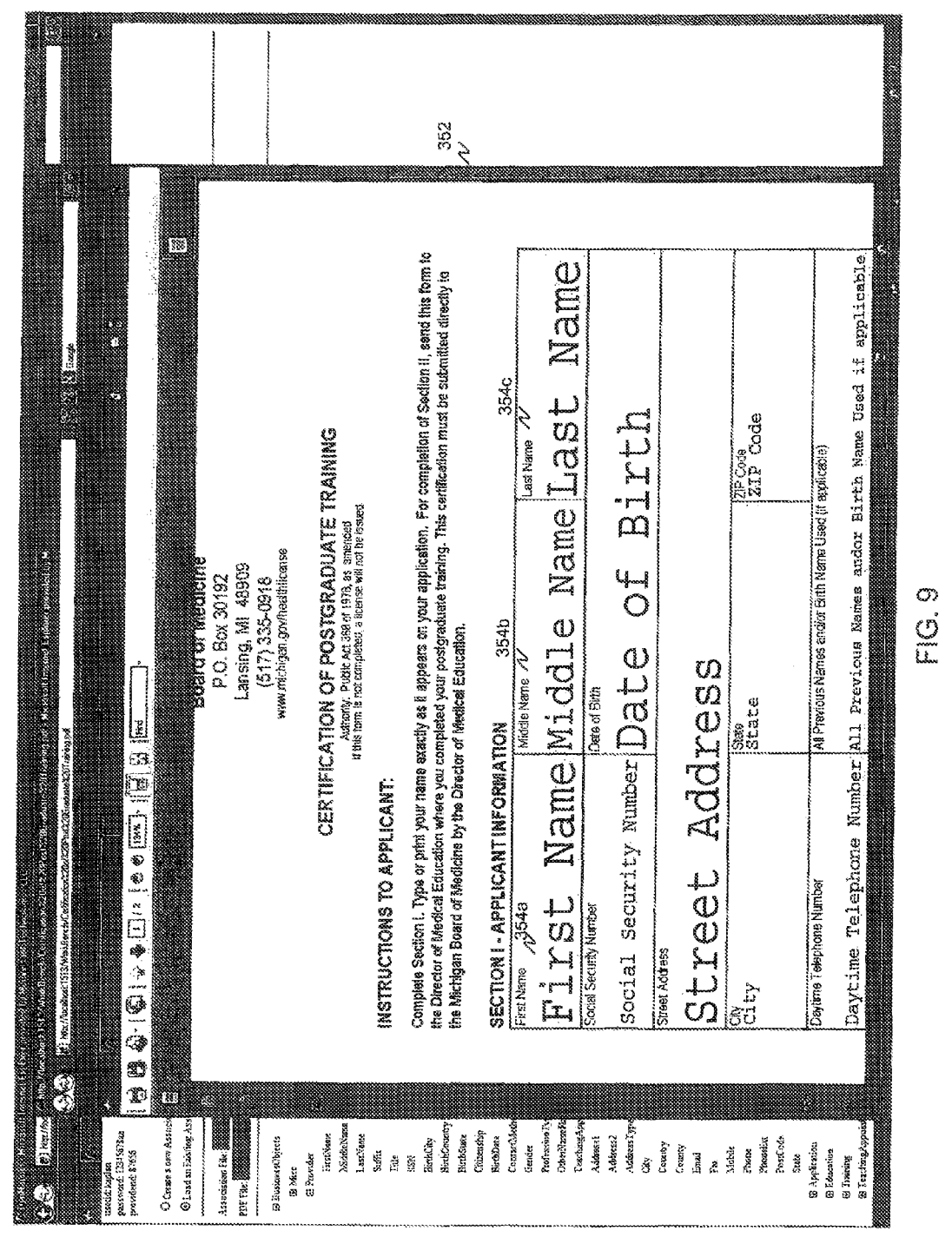

Selection of a particular form from the forms list and selecting an analyze button 382 retrieves the encoding file containing all the fields of the form, and causes the fields to be displayed in a field list area 362 of the display. In addition, a form viewer is invoked for displaying the selected form is a second portion of the same display, or alternatively, on a separate window. FIG. 9 is a screen shot of an exemplary screen/window 352 displaying a form that has been selected for mapping. According to one embodiment of the invention, the form includes one or more tillable fields 354a-354e, each of which is associated with a unique field ID, as identified in the corresponding encoding file.

The relevant object(s) from the common class object model 20 is displayed by the GUI as a hierarchical object tree 356 (which is similar to the hierarchical tree of FIG. 3). One or more attributes and properties associated with the particular object may be collapsed from view until selected by the mapping user.

In step 302, the mapping engine 100a identifies, based on input provided by the user, the fields in the displayed form. In step 304, the mapping engine further identifies, based on input provided by the user, the attributes and properties that are to be mapped to the identified fields, from the displayed hierarchical tree. In step 306, the mapping engine generates a map file with the mapping data, and stores the map file in the data storage device in step 308. Thus, unlike the prior art requiring manual coding of each form to create a one-to-one mapping of a form field directly into a database field, the present invention provides a single common object model that may be reused for various forms to automate and facilitate the mapping process.

According to one embodiment of the invention, the mapping of objects of the model to fields of a form is accomplished by dragging and dropping the objects and the fields into a predefined mapping area so as to cause an association between the objects and fields in the area. Alternatively, the mapping may be accomplished by dragging and dropping the displayed objects to corresponding fields of the displayed form, or vice versa. In yet another embodiment, other visual mechanisms for identifying objects and fields to be mapped to one another may be provided by the GUI instead of the drag-and-drop mechanism, such as, for example, highlighting the objects and fields that are to be mapped.

According to the embodiment displayed in FIG. 8, a field from the field list area 362 is selected, dragged, and dropped into a field ID portion 358 of a mapping area provided by the GUI. Similarly, one or more corresponding business objects from the object tree 365 are selected, dragged, and dropped into a business object portion 360 of the mapping area to cause the mapping of the selected form field with the selected business object(s).

If multiple data entries are stored for a particular business object, a selection/row# option 366 may be selected to indicate the data entry that is to be selected for pre-populating the form. For example, multiple telephone numbers may be stored in multiple rows for a "Phone" business object. A user may indicate via the selection/row# option 366 the row storing the telephone number that is to be used for purposes of pre-populating the form.

In addition, a user may define the type of association or mapping to be made between a form field and object(s) appearing in the mapping area. According to one embodiment of the invention, the association or mapping may default to be a one-to-one connection. However, more complex associations may be selected by the user, such as for example, a particular type of conversion (also referred to as derivation or transformation) from conversion drop down list 364, or a particular type of aggregation from an aggregation drop down list 368. For example, the user may select a connector from the conversion drop down list 364 that indicates a derived association that may be defined by one or more functions.

In the event a derived association is selected, the mapping engine is configured to prompt for information that is needed for deriving a value to be filled into one or more field(s) of the form, based on corresponding information in the object model. As an example, a user may indicate a derived association for a gender object where the model requires the gender value to be "male" or "female." However, in the corresponding gender field of the form being mapped, the acceptable values may be "1" for male and "2" for female. In indicating that the association for the gender object is a derived association, the user specifies that "male" should be converted to a value of "1," and that "female" should be converted to a value of "2," when pre-populating this particular field of the form.

The selected connector may also identify a transformation rule for transforming an aspect of the stored values. For example, the transformation rule may be to always capitalize the first letter of the value when pre-populating the corresponding field, or perform some other transformation in the formatting of the data being entered into the form. For example, data may have to be truncated if it exceeds the size of a field to which it is being inserted.

Figure 10:
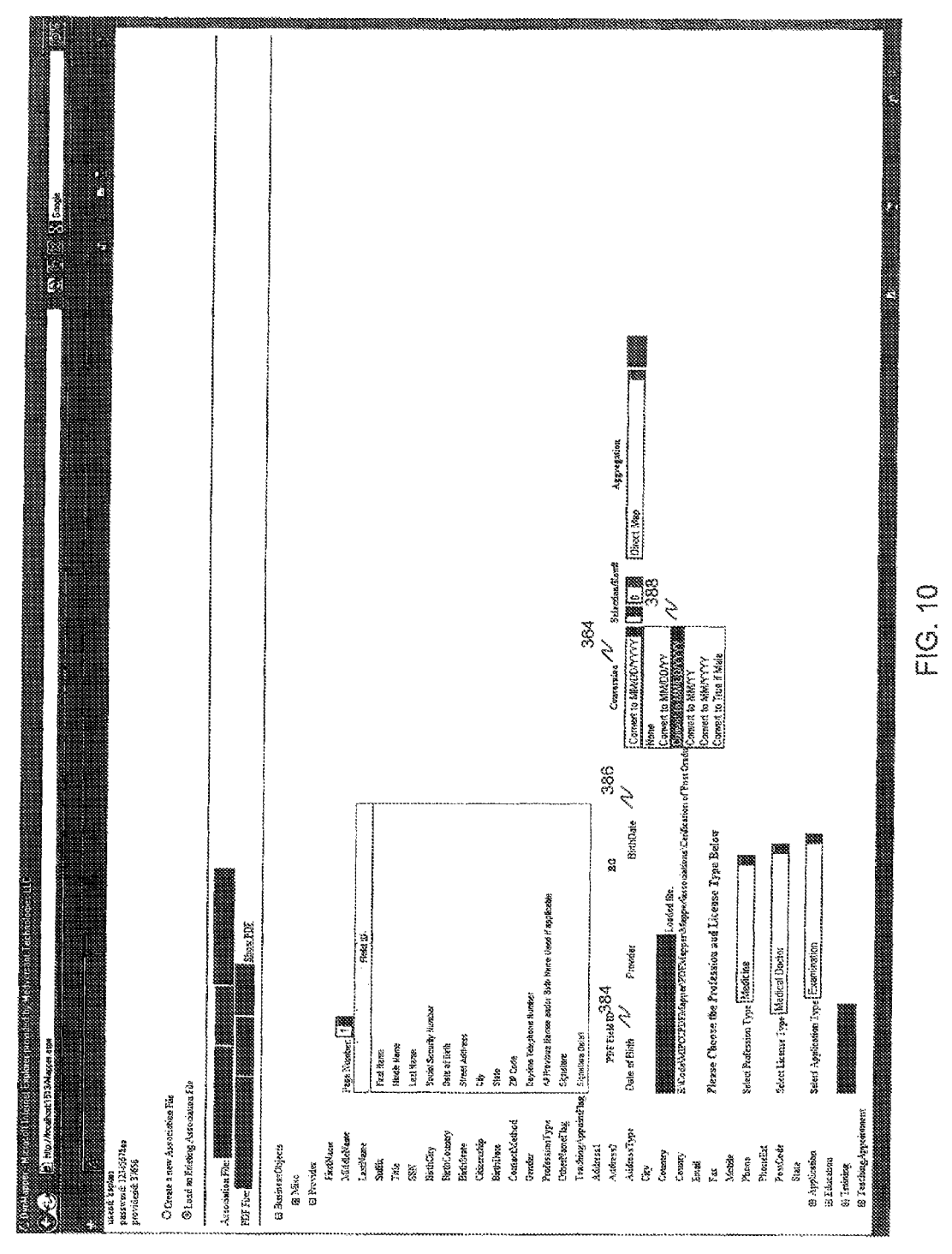

FIG. 10 is a screen shot of an exemplary screen with a list of conversion options in the conversion drop down list 364. According to one embodiment, conversions, derivations, and transformations are all simply referred to as conversions. In the screen shot of FIG. 10, the user has indicated that a date of birth field 384 of the form is to be mapped to a provider's birth date object 386. The user further has indicated that the type of mapping is a specific type of conversion of the business object data by selecting a conversion rule 388 from the conversion drop down list 364. The selected conversion rule 388 instructs the running engine 100c that when populating the date of birth field in the form with the birth date data stored in the common object model, the running engine 100c is to invoke a set of associated computer instructions for running an algorithm that converts the stored data into a MM/DD/YYYY format before populating the field, if not already in this form in the database. Such an algorithm will be apparent to a person of skill in the art.

Referring again to FIG. 8 if multiple objects have been selected from the object tree 356 for mapping into a single from field, the user may select a particular type of aggregation rule from an aggregation drop down list 368. According to one embodiment of the invention, the aggregation rule controls how the data aggregated from the different objects are to be joined and displayed on the mapped field when it is time to populate this field.

Figure 11:
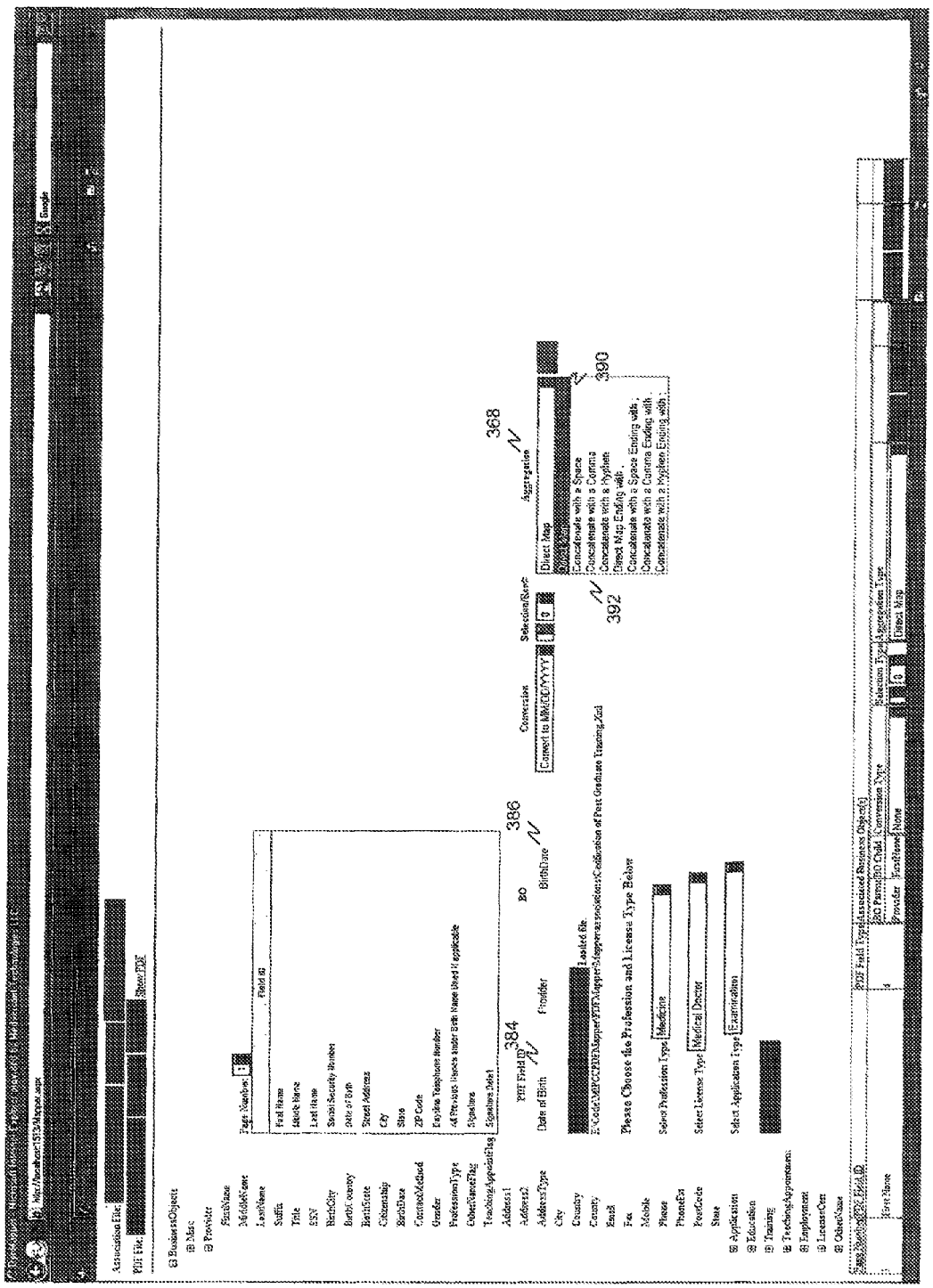
FIG. 11 is a screen shot of an exemplary screen with a list of aggregation options in an aggregation drop down list, according to one embodiment of the invention.

FIG. 11 is a screen shot of an exemplary screen with a list of aggregation options in the aggregation drop down list 368. In the example provided, the user has indicated a direct mapping 390 of the data stored for the provider's birth data object 386 and the date of birth field 384 of the form. However, if multiple business objects are to be mapped to a single form field, the user may select another type of aggregation mapping provided by the drop down list 368. For example, the name field of a particular form may require that the first and last names be entered together into the same field, separated by a comma. In this case, the user selects the first name and last name objects from the object tree, and further selects the appropriate aggregation rule 392 from the aggregation drop down list 368 indicating how the aggregated data from the two business objects are to be displayed in the mapped field. In the example, the selected aggregation rule 392 instructs the running engine 100c that when populating the name field of the form with the first and last name data stored in the common object model, the running engine 100c is to invoke a set of associated computer instructions for running an algorithm that concatenates the first and last names, with a comma in between. Such an algorithm will be apparent to a person of skill in the art.

According to one embodiment of the invention, at least the field ID portion 358 and business object portion 360 provided by the GUI is referred to as a mapping area. According to one embodiment of the invention, the mapping area may also include the selection/row# option 366, conversion drop down list 364, and aggregation drop down list 368.

Figure 12:
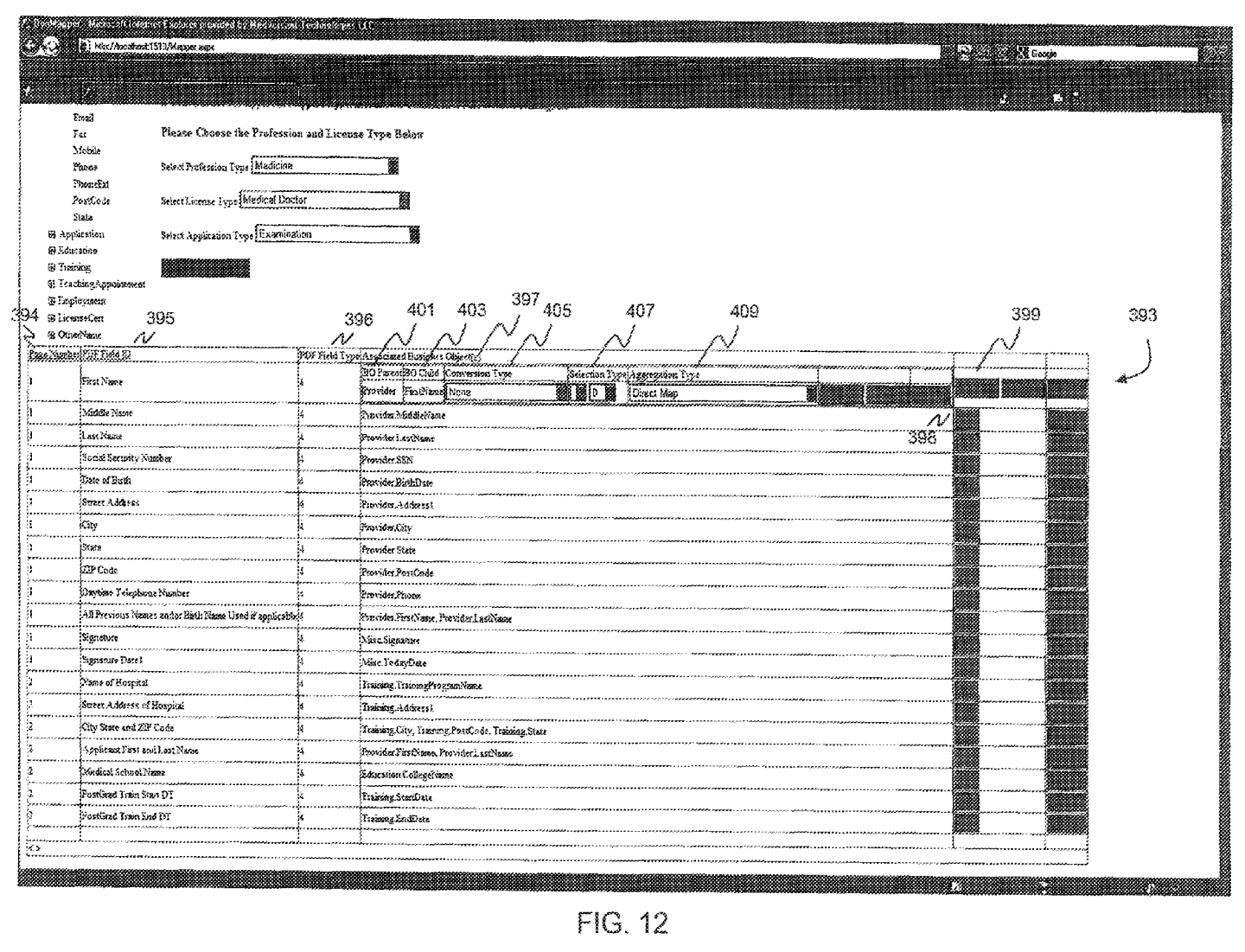

Referring again to FIG. 8, selecting a save button 370 causes the generating of a mapping entry in a mapping table 393 for storing the mapping information. A more detailed screen shot of an exemplary mapping table is depicted in FIG. 12. According to one embodiment, each entry of the mapping table identifies the current mapping schema including a page number 394 of the form that was mapped, and the field ID 395 and field types 396 mapped for each page. The field ID may indicate the name of the mapped field. The field type may indicate the type designation of the field, such as, for example, numbers indicating whether the field is a textbox, multiple choice, checkbox, dropdown, or the like. Each entry also identifies one or more business objects 397 mapped to each field ID. Selection of an edit button 398 displays detailed information of the mapped business object(s), such as for example, identification of the current parent 401 and child 403 objects, current conversion type 405, current selection type 407, and current aggregation type 409, with an option to update 399 the current mapping information.

Figure 13:
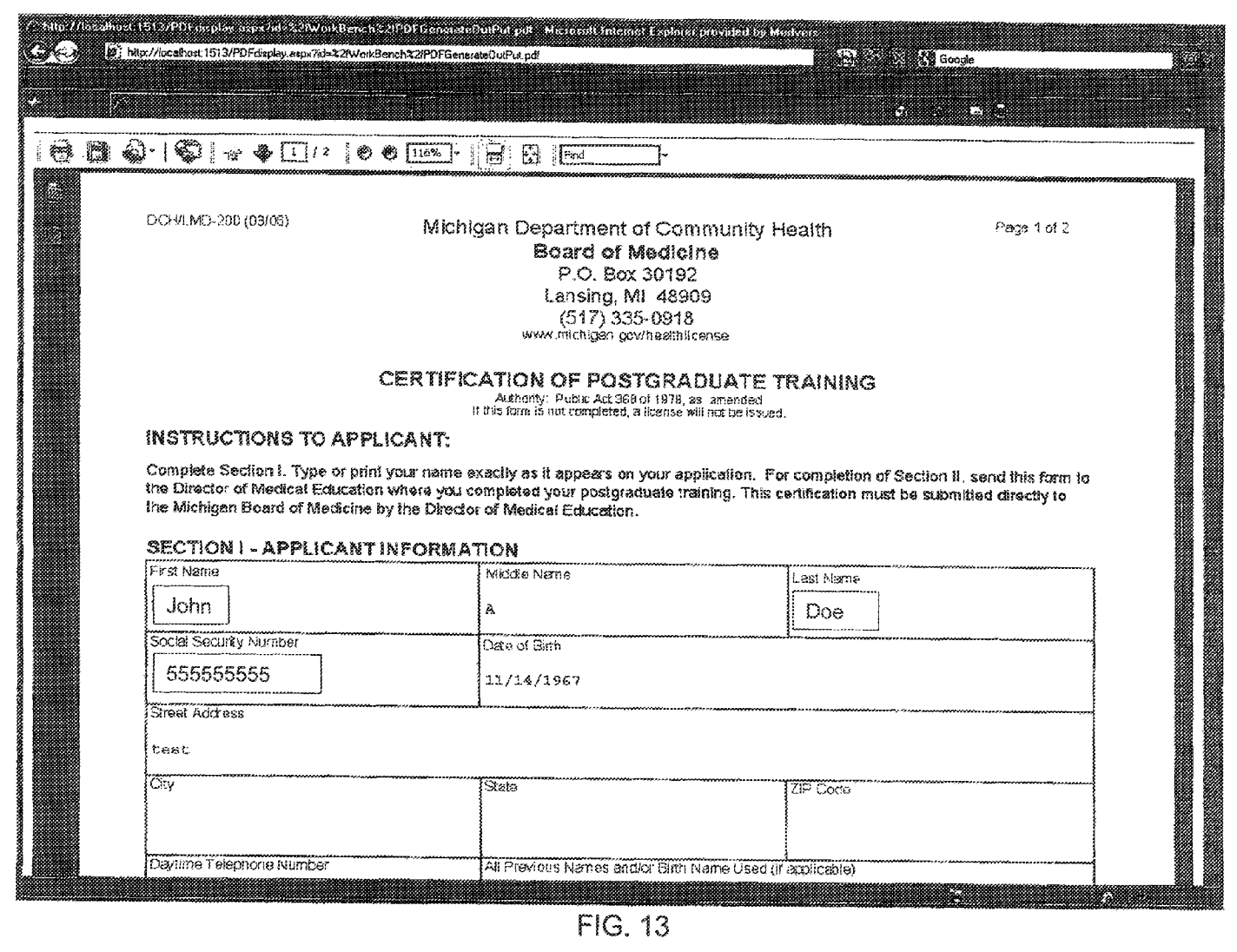

A preview or generate PDF button 380 (FIG. 8) provided by the GUI allows a user to preview the form derived from the mapped schema. In this regard, selection of the generate PDF button 380 causes retrieval of sample data from the object model, and then a display of the transformed data in the mapped form with the data automatically filled in based on the selected mapping. In this manner, the mapping user may verify that the mapping is correct. FIG. 13 is a screen shot of the form depicted in FIG. 9, with exemplary data filled in according to the mapping schema in the mapping table 393 of FIG. 12. If any of the fields was mapped incorrectly, the mapping user may change the mapping information in the mapping table 393 by selecting the edit button 398 for the erroneously mapped field.

Upon verification that the mapping is correct, the mapping user selects a save to file button 411 (FIG. 8) to store the mapping table 393 into a designated map file (also referred to as association file). According to one embodiment of the invention, the map file is stored in the data storage device 108 along with its metadata. Such metadata may include, for example, a form ID identifying the form that was mapped, a version of the form, healthcare entity providing the form, information on the person generating the map file, a date on which the map file was generated, status of the map file as being approved or pending, and the like. According to one embodiment of the invention, the map file is an XML file, although other types of encoding files conventional in the art may be used in lieu of an XML file.

In other embodiments of the invention, a publish button (not shown) may also be provided to move the generated map file to a staging area of the data storage device 108. According to this embodiment, all map files in the staging area require approval by a reviewer/administrator. The server 100 may provide a management portal that a mapping reviewer/administrator can access via the user device 112 to review and approve all map files in the staging area. Once the map file is marked as being approved upon indication of approval by the reviewer/administrator, the map file may be transferred from the staging to a mapping database of the data storage device 108.

Embodiments of the present invention are also configured to efficiently handle updates to forms as new versions of forms are introduced to replace older versions. According to one embodiment of the invention, the mapping engine may compare the fields of the old form with the fields of the new form, and upon a discrepancy in the fields, highlight the fields that are different in the new form. In many cases, the changes will be minor. Thus, instead of having a user re-create the entire mapping schema for a new version of the form, the mapping engine provides the option to copy a previous mapped schema for reusing any of the mapping data that remains intact. Unlike prior art methodologies where any updates to forms requires new programming to manually code each field to a corresponding database field, embodiments of the present invention allow the reusing of previous mapping schema for improved efficiency of the mapping process.

A person of skill in the art should appreciate that the visual mapping provided via the embodiments of the present invention allow the mapping to be carried out in a user-friendly, intuitive manner, that does not require low level manipulation of database fields or other programming knowledge. As a result, the mapping tool provided by embodiments of the present invention is more scalable for dealing with the vast amount of different forms in the healthcare industry. In addition, embodiments of the present invention handle changes to forms in a manner that maximizes the reusing of prior mapping data, again making the mapping tool highly efficient and scalable in handling those changes.

Figure 5:
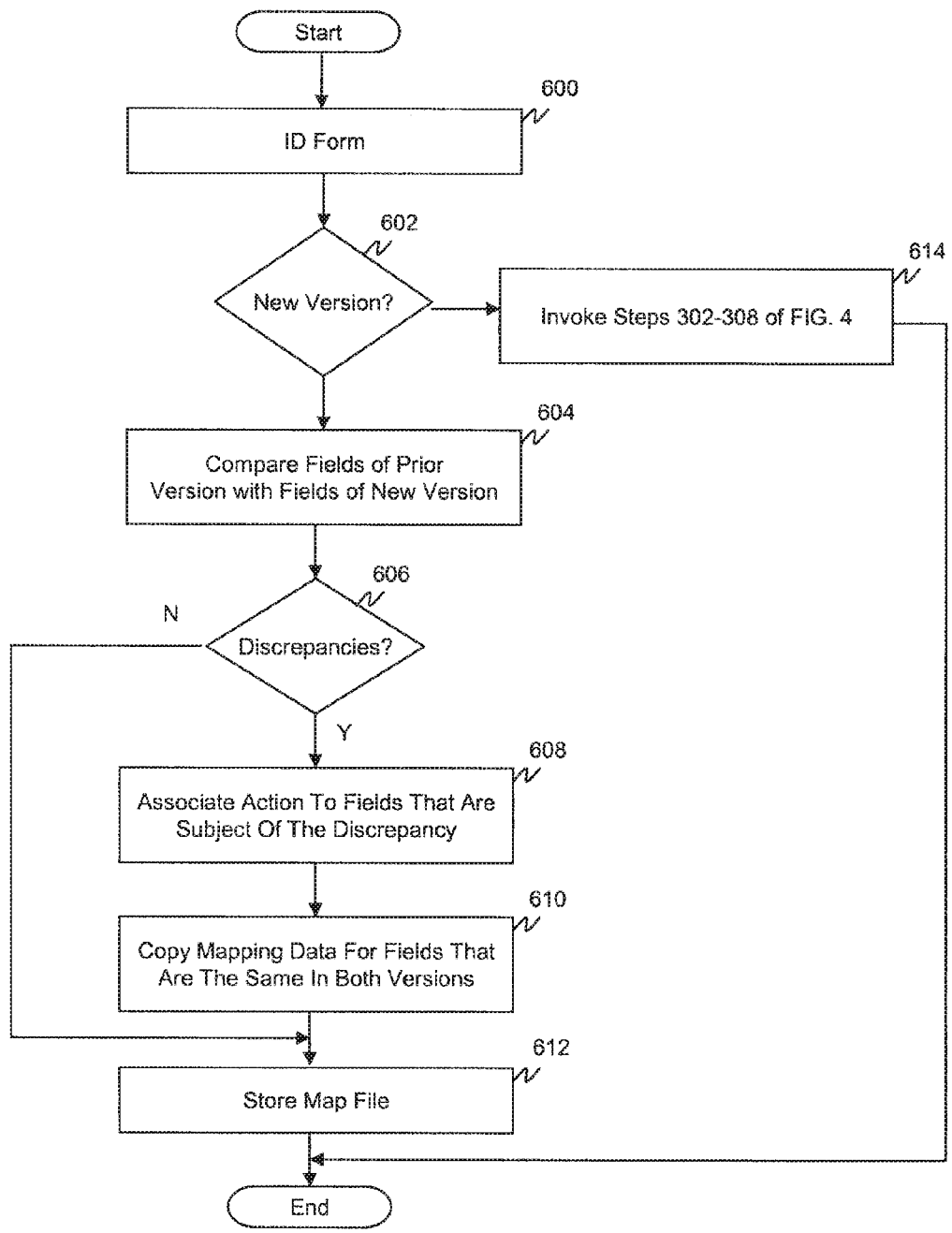
FIG. 5 is a flow diagram of a process executed by a mapping engine to generate a map file for a new version of a form that may contain updates, according to one embodiment of the invention.

FIG. 5 is a flow diagram of a process executed by the mapping engine 100*a* to generate a map file for a new version of a form that may contain updates, according to one embodiment of the invention. The process may be described in terms of a software routine executed by the processor in the server 100 based on instructions stored in the server's memory. A person of skill in the art should recognize, however, that the routine may be executed via hardware, firmware (e.g. via an ASIC), or in any combination of software, firmware, and/or hardware. Furthermore, the sequence of steps of the process is not fixed, but can be altered into any desired sequence as recognized by a person of skill in the art.

In step 600, the mapping engine 100*a* identifies a form that requires mapping. In this regard, a user may select the form that is not marked as being mapped from the form library, and transmit his selection to the mapping engine. In another embodiment, the mapping engine 100*a* may periodically check the status of the forms in the form library, and automatically identify those forms that require mapping. The mapping engine 100*a* may then prompt a user to initiate mapping of those forms. In yet another embodiment, the prompt to the user to initiate mapping of the new form may occur as soon as the form is uploaded into the form library.

Once a determination is made that a mapping should be conducted, and the form that is the subject of such mapping has been identified, the mapping engine 100*a* determines in step 602 whether the identified form is a new version of a pre-existing form. If the answer is NO, steps 302-308 of the process depicted in FIG. 4 is invoked in step 614.

If the answer is YES, and the form is a new version of a pre-existing form that has an older mapped version, the mapping engine 100*a* proceeds to compare the fields of the prior version with the fields of the new version. In this regard, the mapping engine 100*a* retrieves the encoding file (e.g. an XML file) for the prior version and the encoding file of the new version, and performs a compare operation for identifying discrepancies in the two files. Such a discrepancy may indicate a field ID and field name in the old version which is no longer found in the new version, or vice versa.

A determination is thus made in step 606 as to whether discrepancies were found during the compare operation. If the answer is YES, the mapping engine 100*a* associates one or more actions to fields that are the subject of the discrepancy. For example, if a field was added to the new version of the form, the field might be displayed in a highlighted form to notify the mapping user that the field needs to be manually mapped. Default text may also be added to the highlighted field. In response, the mapping user may, via a draft-and-drop process discussed above with respect to FIG. 4, map the added field to a corresponding object in the object model, and store the generated mapping data in a new map file.

If however, a field that used to exist in the old version of the fox in is no longer present in the new version, the mapping engine may simply display a notification to this effect for the mapping user.

In step 610, the mapping engine 100*a* proceeds to copy the mapping data for the fields that are the same in both versions of the form. In this regard, the mapping engine retrieves the map file for the prior version of the form using the reference information for the prior version of the form, and copies the mapping data for the fields that have not changed from the old version to the new version. The copied mapping data is then stored in step 612 into the new map file.

Once a form has been mapped to a common object model, the fields of the form may be automatically populated/completed based on information stored with reference to the common object model.

Figure 6:
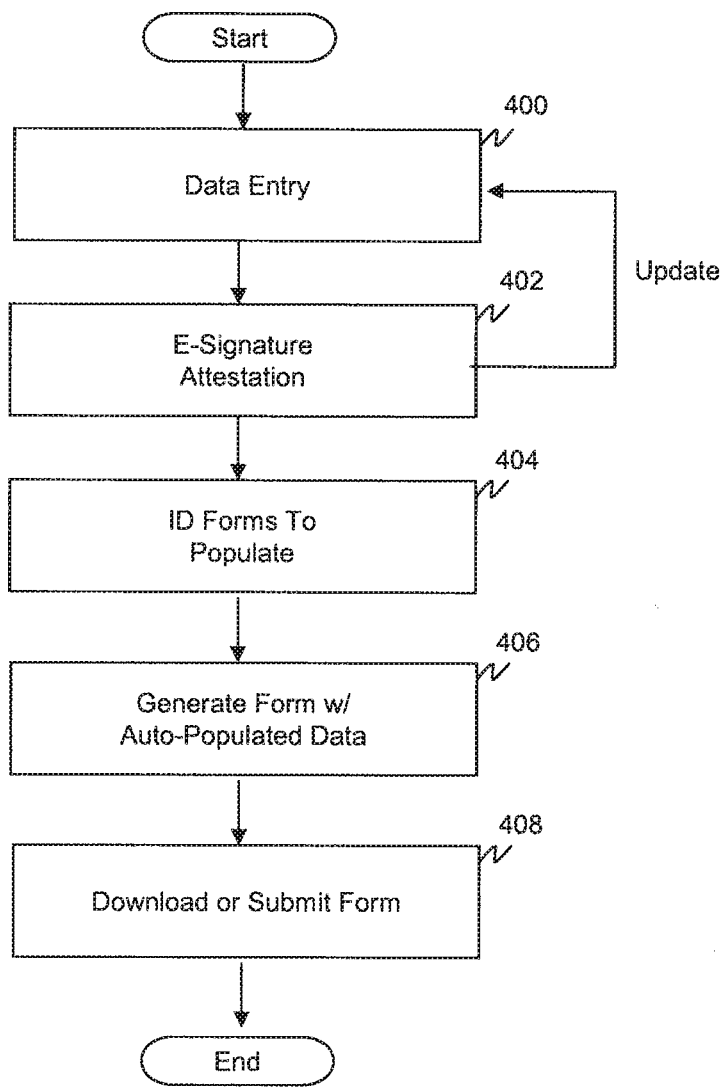
FIG. 6 is a flow diagram of an overall process for populating the object model with information of a particular provider and automatically generating a form with the fields pre-populated with the provided information according to one embodiment of the invention.

FIG. 6 is a flow diagram of an overall process for populating the object model with information of a particular provider and automatically generating a form with the fields pre-populated with the provided information according to one embodiment of the invention. The process may be described in terms of a software routine executed by the processor in the server 100 based on instructions stored in the server's memory. A person of skill in the art should recognize, however, that the routine may be executed via hardware, firmware (e.g. via an ASIC), or in any combination of software, firmware, and/or hardware. Furthermore, the sequence of steps of the process is not fixed, but can be altered into any desired sequence as recognized by a person of skill in the art.

In step 400, a provider or any other user of the system accesses a provider portal, such as, for example, one of the web portals 100*b* hosted by the server 100, to further access an application in the portal that captures data for populating the common object model 20. According to one embodiment of the invention, the application provides a universal online form generated based on the common object model, that prompts the provider for information for populating the common object model. In this case, the provider himself is the source of the data, and may provide such data via any input device coupled to the provider device 102. According to one embodiment of the invention, the universal online form is a web page or a set of web pages prompting a user to enter specific information pertaining to the user.

In other embodiments, the data is provided by one or more information sources 106 such as, for example, schools, hospitals, insurance carriers, government agencies, and the like. The information sources may provide the data in electronic form (e.g. CD-ROM, email, scan, fax, etc.), via paper-based forms, or directly enter the data online via the web portal 100b. The data may also be gathered automatically from the information sources 106 via use of web crawlers and the like. In yet another embodiment, a form that has been mapped to the common object model may be source of the data for populating the common object model. That is, instead or in addition to filling out the universal form, a user may also directly fill out a specific type of form for which mapping data exists. The form may be filled out online via the web portal 100b, or offline first, and a copy of the completed form provided to the server in electronic form (e.g. CD-ROM, email, scan, fax, etc.). All or portions of the common object model may then be populated based on the information provided in the specific form.

In step 402, the user provides his or her e-signature for being stored in the data storage device 108, along with the provider's attestation that the information being provided is accurate and current. The information provided to populate the common object model may also be verified as described in the above-referenced U.S. Pat. No. 7,529,682. The provider may also periodically update the information as needed, with or without the benefit of alarms or prompts by the server.

According to one embodiment of the invention, the server 100 may be configured to take all or a portion of the data used to populate the common object model and search a plurality of different information sources 106 to verify that the information is accurate. For example, the server 100 may be configured to compare information stored at the information sources with the information provided by the provider for determining whether there are any inconsistencies. Such information sources 106 may be social networking sites, information databases, or any other body of information conventional in the art. Any mechanism for identifying, accessing, and comparing the information may be utilized as will be apparent to a person of skill in the art. The server 100 may be configured to transmit an alarm to the provider, healthcare entities, information sources, governmental agency, or any other entity identified by the server, upon a discrepancy in the information being compared.

According to one embodiment of the invention, the provider may need a form generated and submitted to a healthcare entity. For example, the provider may need to submit an enrollment form to enroll in a particular health plan, and may access the provider portal to request such form. Other healthcare entities may also trigger the generating of forms. In either scenario, the provider portal invokes the runtime engine 100c and identifies, in step 404, a particular form to populate and generate.

In step 406, the runtime engine generates the form with automatically populated data obtained from the provider object model. In this regard, the runtime engine may assume that the form is to be automatically populated with the data stored in the common object model upon the user selection of the form, which then eliminates the need for manual filling out of the fields by the user. Alternatively, the user may be given the option to manually enter all or some of the data if the user does not want the form automatically populated.

In step 408, the runtime engine receives a request to download the form to the provider device, or to automatically submit the form to a recipient that interfaces with the server, such as, for example, a healthcare entity device 104. According to one embodiment of the invention, the interface is an application program interface (API) that allows all form data to be submitted directly to the recipient via an API channel according to conventional mechanisms.

Figure 7:
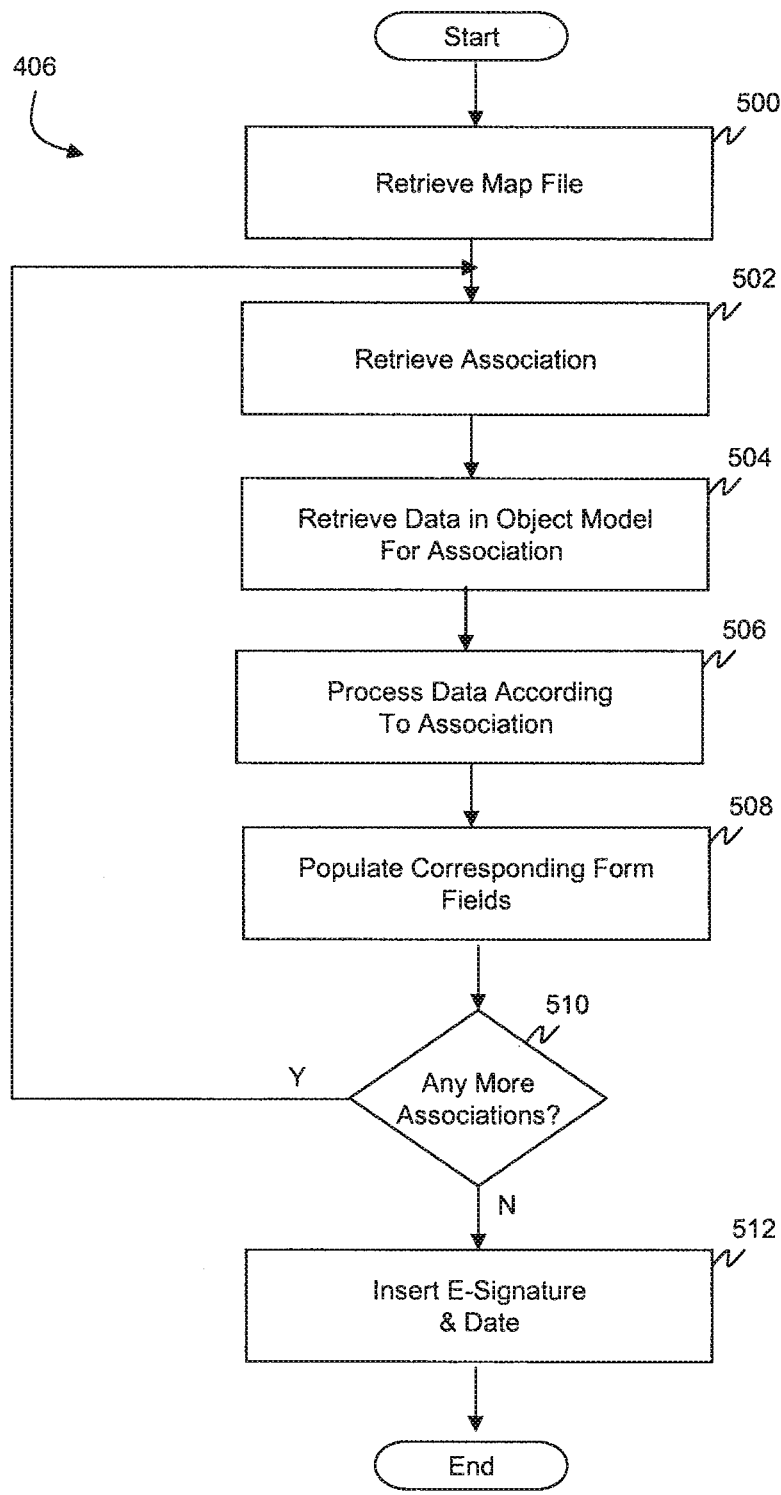
FIG. 7 is a more detailed diagram of a step for generating a form with automatically populated data according to one embodiment of the invention.

FIG. 7 is a more detailed diagram of step 406 of generating a form with automatically populated data according to one embodiment of the invention.

In step 500, the runtime engine uses the form ID corresponding to the selected form, and retrieves a corresponding map file from the mass storage device 108.

In step 502, the runtime engine retrieves a stored association from the map file. In this regard, the association identifies the one or more object attributes or properties mapped to a particular field of the form, along with any transformation or aggregation functions that are to be performed for the association.

In step 504, the runtime engine uses an instantiation of a data access layer and uses the layer components to retrieve data stored for the identified object attribute or property.

In step 506, the runtime engine processes the retrieved data according to the retrieved association. In this regard, the runtime engine identifies any conversion and/or aggregation rule indicated for the association, and invokes the appropriate algorithm(s) for processing the retrieved data according to the conversion and/or aggregation rule. The processing may be as simple as making a copy of the retrieved data for entering the data as-is into the corresponding form, such as, for example, if the aggregation is a direct mapping of the data. For other types of conversions and/or aggregations, the algorithm may require transformation, derivation, and/or concatenating of the data, as well as inserting spaces or text (e.g. hyphens, commas, semi-colons, etc.).

In step 508, the runtime engine uses the processed data to automatically populate the corresponding form field.

In step 510, a determination is made as to whether there are any other associations in the map file that need to be processed for auto-populating the form. If the answer is YES, the runtime engine returns to step 502 to process the other associations. Otherwise, if the answer is NO, the runtime engine pulls, in step 512, a stored e-signature of the provider for whom the form is generated, as well as a date, and enters this information into corresponding fields of the form. The form is then ready to be displayed on the provider device 102 for review by the provider. The provider may review and make any needed updates to the pre-populated information, and/or manually enter information for any fields that have not been automatically pre-populated. The form is then ready to be downloaded to the provider, or to be submitted directly to a healthcare entity coupled to the server. In this regard, the web portal 100b may provide a "download" option which causes transmitting a copy of the filled form for storing in a data store coupled to the provider device. The web portal 100b may also provide a "submit" option which prompts the user to enter information of the entity (e.g. an email address) who is to receive a copy of the filled form.

Although this invention has been described in certain specific embodiments, those skilled in the art will have no difficulty devising variations to the described embodiment which in no way depart from the scope and spirit of the present invention. Furthermore, to those skilled in the various arts, the invention itself herein will suggest solutions to other tasks and adaptations for other applications. For example, although may of the forms used in the exemplary embodiments relate to healthcare forms, a person of skill in the art should recognize that embodiments of the present invention applies to other fillable forms used in other fields. It is the Applicant's intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

What is claimed is:

1. A computer-implemented method for automatically mapping and populating fields in any selected electronic form specific to the field of healthcare from a common object model for any one of a multiplicity of diverse healthcare provider information with minimal manual input by the user, the method comprising the steps of:
    displaying a plurality of objects from the common object model as a hierarchical object tree for a selected healthcare provider with the object model including detailed information relative to each healthcare provider and with the detailed information for the selected healthcare provider being represented by attributes and properties of the selected healthcare provider inclusive of at least gender, type of medical license, professional degree and work history;
    displaying a plurality of fields of the electronic form;
    receiving user selection from displayed objects of the common object model for the selected healthcare provider;
    displaying the selected objects in a mapping area;
    receiving user selection of fields from the displayed fields of the electronic form;
    displaying the selected fields in the mapping area;
    identifying a type of association between each of the selected objects in the mapping area and each of the selected fields in the mapping area with the identified type of association being selected from a group consisting of: a one to one connection between selected object and form field when it exists, and a conversion, including a derived association, a transformative association and an aggregation based upon an evaluation and determination of the attributes and properties of the selected healthcare provider from the displayed hierarchical object tree, when a one to one connection between selected object and form field does not exist; and
    generating a mapping entry in a map file mapping the objects in the mapping area to the fields in the mapping area based on said attributes and properties of the selected healthcare provider and the identified type of association,
    wherein the map file is stored and configured to be retrieved for use in automatically populating the plurality of selected fields in a selected electronic form from the stored map file for a selected healthcare provider and
    wherein the user selection of the displayed objects involves dragging and dropping each of the selected objects to the mapping area, and the user selection of displayed fields involves dragging and dropping each of the selected displayed fields to the mapping area.

2. The method of claim 1, wherein the displaying the plurality of objects includes displaying identifiers for the objects in a list format.

3. The method of claim 1, wherein the type of association includes an aggregation rule for aggregating data stored for the plurality of objects in the mapping area, when populating the field on the form mapped to the plurality of objects.

4. The method of claim 3, wherein the type of association further includes a conversion rule for converting an aspect of data stored for the one or more objects in the mapping area, when populating the field on the form mapped to the one or more objects.

5. The method of claim 4, wherein the converting is converting a format of the data.

6. A computer-implemented method for automatically mapping and populating an electronic form specific to the field of healthcare from a common object model for any one of a multiplicity of diverse healthcare providers with the object model including detailed information relative to each healthcare provider and with the detailed information for the selected healthcare provider being represented by attributes and properties of the selected healthcare provider inclusive of at least gender, type of medical license, professional degree and work history, the method comprising the steps of:
    receiving data pertaining to a user;
    populating said common object model based on the received data;
    receiving user selection of one electronic form to be populated, the selected form including one or more fields;
    identifying a type of association between each of the selected objects in the mapping area and each of the selected fields in the mapping area, with the identified type of association being selected from a group consisting of a one to one connection between selected object and form field when it exists, and a conversion, including a derived association, a transformative association and an aggregation based upon an evaluation and determination of the attributes and properties from the common object model in the displayed hierarchical object tree when a one to one connection between selected object and form field does not exist;
    storing a map file containing said identified type of association;
    retrieving the map file for the selected form, with the map file mapping each of the fields in the form to objects of the common object model using said identified type of association for the selected healthcare provider
    retrieving data mapped to the fields of the selected form;
    processing the retrieved data file for a given user;
    automatically populating the one or more fields of the form based on the processed data with minimal or no additional manual input of data by the user into the fields of the form; and
    displaying the populated fields on a display device.

7. The method of claim 6 further comprising:
    displaying a universal form corresponding to the common object model; and
    prompting the user to enter information requested on the universal form.

8. The method of claim 6, wherein the type of association includes an aggregation rule for aggregating data from a plurality of objects of the common object model when populating a field mapped to the plurality of objects, wherein the processing aggregates the data according to the aggregation rule.

9. The method of claim 6, wherein the type of association includes a conversion rule for converting an aspect of data stored for one or more objects of the common object model when populating a field mapped to the one or more objects, wherein the processing converts the aspect of the data according to the conversion rule.

10. The method of claim 9, wherein the processing includes converting a format of the data.

11. The method of claim 6, wherein the fields of the selected form is automatically populated based on the processed data without manual input of the data by the user into the fields of the form.

12. A computer apparatus for mapping and populating fields in any selected electronic form specific to the field of healthcare from a common object model for any one of a multiplicity of diverse healthcare providers with the object model including detailed information relative to each healthcare provider and with the detailed information of a selected healthcare provider being represented by attributes and properties of the selected healthcare provider inclusive of at least gender, type of medical license, professional degree and work history, comprising:

a data storage device;

a display device displaying a mapping area;

a processor; and a memory operably coupled to the processor having program instructions stored therein, the processor being operable to execute the program instructions including:

displaying on the display device a plurality of objects of the common object model for a selected healthcare provider;

displaying on the display device a plurality of fields of the selected electronic form;

receiving user selection of one or more of the displayed objects of the common object model;

displaying the selected one or more objects in the mapping area;

receiving user selection of one of the displayed fields of the electronic form;

displaying the selected field in the mapping area;

identifying a type of association between each of the selected objects in the mapping area and each of the selected fields in a mapping area with the type of association selected from the group consisting of a one to one connection between selected object and form field when it exists, and a conversion, including a derived association, a transformative association and aggregation based upon an evaluation and determination of the attributes and properties of the user in said common object model inclusive of at least gender, type of medical license, professional degree and work history, when a one to one connection between selected object and form field does not exist; and generating a mapping entry in a map file of the data storage device mapping the objects in the mapping area to the fields in the mapping area, with each mapping entry being based on the identified type of association, and wherein the map file is stored and configured to be retrieved such that the plurality of selected fields of the selected electronic form will be automatically populated with common data for the objects mapped to the plurality of fields from the stored map file;

wherein the user selection of the displayed objects involves dragging and dropping each of the selected objects to the mapping area, and the user selection of displayed, fields involves dragging and dropping each of the selected displayed fields to the mapping area.

13. The computer apparatus of claim 12, wherein the program instructions for displaying the plurality of objects includes displaying identifiers for the objects in a list format.

14. The computer apparatus of claim 12, wherein the program instructions for identifying the type of association comprises program instructions for:

displaying a list of associations based upon the attributes and properties of the user in said common object model; and receiving a user selection of one of the associations from the list.

15. The computer apparatus of claim 12, wherein the type of association indicates mapping a plurality of the objects in the mapping area, to the fields in the mapping area.

16. The computer apparatus of claim 15, wherein the type of association includes an aggregation rule for aggregating data stored for the plurality of objects in the mapping area, when populating the field on the form mapped to the plurality of objects.

17. The computer apparatus of claim 16, wherein the type of association further includes a conversion rule for converting an aspect of data stored for the one or more objects in the mapping area, when populating the field on the form mapped to the one or more objects.

18. The computer apparatus of claim 17, wherein the computer instructions for converting includes computer instructions for converting a format of the data.

* * * * *